United States Patent [19]

Bank

[11] Patent Number: 5,110,974
[45] Date of Patent: May 5, 1992

[54] THERMAL DISPROPORTIONATION OF ARYLHALOSILANES

[75] Inventor: Howard M. Bank, Freeland, Mich.

[73] Assignee: Dow Corning Corporation, Midland, Mich.

[21] Appl. No.: 782,178

[22] Filed: Oct. 24, 1991

[51] Int. Cl.$^5$ ............................................... C07F 7/08
[52] U.S. Cl. .................................................... 556/469
[58] Field of Search ........................................ 556/469

[56] References Cited

U.S. PATENT DOCUMENTS

| | | | |
|---|---|---|---|
| 2,611,775 | 9/1952 | Barry | 556/469 X |
| 2,730,540 | 1/1956 | Sauer | 556/469 |
| 2,746,981 | 5/1956 | Wagner | 260/448.2 |
| 3,637,780 | 1/1972 | Bazouin et al., | 556/469 |
| 3,655,710 | 4/1972 | Bazouin et al. | 556/469 |
| 4,746,752 | 5/1988 | Lepage et al. | 556/469 |

FOREIGN PATENT DOCUMENTS 62-263189 11/1987 Japan .

OTHER PUBLICATIONS

Eaborn et al.; The Interaction of Aryl-Silicon Compounds and Substituted Silyl Radicals J. Organometal. Chem 4:489 (1965).
Gilman et al.; Disproportionation Reaction of Diphenylsilane in the Absence of any Added Catalyst J. Org. Chem. 23:326-328 (1958).

Primary Examiner—Paul F. Shaver
Attorney, Agent, or Firm—William F. Boley

[57] ABSTRACT

The present invention is a process for the thermal disproportionation of arylhalosilanes containing at least one hydrogen bonded to silicon. The process involves heating the arylhalosilanes in liquid phase to a temperature within a range of about 250° C. to 450° C. The present process is particularly useful for the disproportionation of phenyldihalosilanes to diphenyldihalosilanes.

12 Claims, No Drawings

THERMAL DISPROPORTIONATION OF ARYLHALOSILANES

BACKGROUND OF INVENTION

The present invention is a process for the thermal disproportionation of arylhalosilanes containing at least one hydrogen bonded to silicon. The process involves heating the arylhalosilanes in liquid phase to a temperature within a range of about 250° C. to 450° C. The present process is particularily useful for the disproportionation of phenyldihalosilanes to diphenyldihalosilanes.

It is known that disproportionation of monoaryldichlorosilanes occurs in the presence of Friedel-Crafts type catalysts. For example. Wagner. U.S. Pat. No. 2,746,981, issued May 22. 1956, describes a process for the disproportionation of an aryldichlorosilane containing one aryl group and one hydrogen group. by heating the aryldichlorosilane to a temperature of at least 50° C. and a pressure not to exceed atmospheric in the presence of a Friedel-Crafts type catalyst taken from the class consisting of aluminum chloride and boron chloride, and recovering a diarydichlorosilane.

Japanese Patent 62263189, Published Nov. 16, 1987, describes the use of Lewis acid compounds for the disproportionation of aryldihalosilanes under reduced pressure. The catalysts used are described as Lewis acid compounds such as metal halides and aryl metal compounds. Examples of catalysts described in the Japanese patent are aluminum chloride, aluminum bromide, triphenylborane, and tolylborane.

In general, these processes involving the use of catalyst require that the catalyst either be removed or neutralized prior to distillation to separate desired product. If the catalyst is not removed, the desired product can be disproportionated during the distillation process. reducing process yield. In addition, catalysts such as $AlCl_3$ easily sublime coating the processing equipment. Therefore, it is an objective of the present invention to provide a disproportionation process that does not present these problems typically associated with the use of catalysts.

Gilman et al., J. Org. Chem. 23:326-328 (1958), describes the uncatalyzed disproportionation of $Ph_2SiH_2$ at 100° C. to 300° C. at atmospheric pressure.

Eaborn et al., J. Organometal. Chem. 4:489 (1965), describes a process where phenyltrimethylsilane and trichlorosilane are reacted at 500° C. in the gas phase to give phenyltrichlorosilane and trimethylsilane.

The present process comprises the thermal disproportionation of arylhalosilanes containing at least one hydrogen atom bonded to silicon by heating to a temperature of 250° C. to 450° C. in the absence of a catalyst. The process avoids the aforementioned problems typically associated with the use of catalysts to disproportionate arylhalosilanes.

SUMMARY OF INVENTION

The present invention is a process for the thermal disproportionation of arylhalosilanes containing at least one hydrogen bonded to silicon. The process involves heating the arylhalosilanes in liquid phase to a temperature within a range of about 250° C. to 450° C.. The present process is particularily useful for the disproportionation of phenyldihalosilanes to diphenyldihalosilanes.

DESCRIPTION OF INVENTION

The present invention is a process for the thermal disproportionation of arylhalosilanes. The process comprises heating arylhalosilanes of formula

$$R_cR^1_aH_bSiX_{4-a-b-c}, \quad (1)$$

in liquid phase, at a temperature within a range of about 250° C. to 450° C., for a reaction time of 0.1 to 18 hours, to effect disproportionation to product arylhalosilanes of formula

$$R_cR^1_dH_fSiX_{4-c-d-f}, \quad (2)$$

where each R is independently selected from a group consisting of alkyl radicals of one to 12 carbon atoms, each $R^1$ is independently selected from a group consisting of aryl radicals and substituted aryl radicals. X is a halogen atom selected from a group consisting of bromide, chloride, and iodide, a=1 or 2, b=1 or 2, c=0 or 1, a+b+c=2 or 3, d=a+1, and f=b-1.

Arylhalosilanes which can be thermally disproportionated by the present process are described by Formula (1). The arylhalosilane can contain zero or one substituent R. Each R is independently selected from a group consisting of alkyl radicals of one to 12 carbon atoms. The radical R can be, for example, methyl, ethyl, propyl, isopropyl, butyl, tertbutyl, and decyl. Preferred is when R is methyl. The arylhalosilane can contain one or two substituents $R^1$, where each $R^1$ is independently selected from a group consisting of aryl and substituted aryl radicals. $R^1$ can be, for example, phenyl, tolyl, xylyl, chlorobenzyl, and dichlorobenzyl. Preferred is when $R^1$ is phenyl. The arylhalosilane can contain one or two substituents X, where X is a halogen atom selected from a group consisting of bromide. chloride. and iodide. The preferred halogen atom is chloride. The arylhalosilane must contain one or two hydrogen atom bound to the silicon atom in order for the disproportionation reaction of the present process to occur.

Examples of arylhalosilanes useful in the present process include: phenyldichlorosilane, diphenylchlorosilane, phenylchlorosilane, methylphenylchlorosilane, ethylphenylchlorosilane, phenyldibromosilane, phenyldiiodosilane, tolyldichlorosilane, and chlorophenyldichlorosilane. The preferred arylhalosilane is selected from the group consisting of phenyldichlorosilane and methylphenylchlorosilane.

The arylhalosilane is heated in the liquid phase at a temperature of within a range of about 250° C. to 450° C.. A preferred temperature for the process is within a range of about 300° C. to 400° C.. The present process can be run in any standard pressure reactor capable of maintaining sufficient pressure to keep the arylhalosilane in the liquid phase at process temperatures. A preferred reactor designed is a continuous flow high pressure coil.

The time required for the disportion reaction to occur depends on the temperature at which the process is conducted. In general, reaction times of 0.1 minutes to 18 hours are useful. Preferred is a reaction time within a range of about 0.5 to 4 hours.

Product arylhalosilanes which can be formed by the present process are represented by Formula (2). above. where R, $R^1$, and X are as previously described. In the described process, two arylhalosilane molecules disproportionate effecting an exchange of an aryl or substituted aryl substituent on one arylhalosilane molecule for a hydrogen on the silicon atom of the other arylhalosilane molecule.

Those skilled in the art will recognize that. as a result of this disproportionation reaction. an arylhalosilane molecule containing an additional aryl or substituted aryl substituent and a second halosilane containing an additional hydrogen will be formed. The inventor believes that this is an equilibrium reaction. where an equilibrium is formed between the arylhalosilane and the product arylhalosilane. Therefore, it may be desirable to separate the equilibrium mixture, by a process such as distillation, and recycle the recovered arylhalosilane back to the process.

Examples of product arylhalosilanes which can be formed by the present process include: diphenyldichlorosilane, diphenylchlorosilane, triphenylchlorosilane, methyldiphenylchlorosilane, ethyldiphenylchlorosilane, diphenyldibromosilane, diphenyldiiodosilane, ditolyldichlorosilane, and di(chlorophenyl)dichlorosilane. The preferred product arylhalosilane is selected from the group consisting of diphenyldichlorosilane and diphenylmethylchlorosilane.

To facilitate understanding of the present invention, the following examples are provided. The examples are provided for illustration only and are not intended to limited the claims herein.

EXAMPLE 1

The thermal disproportionation of phenyldichlorosilane ($PhHSiCl_2$) at 300° C. was evaluated. The evaluation was carried out in sealed. 8 mm by 25 cm. Pyrex Brand tubes. Prior to sealing and use. the Pyrex tubes were dried at 120° C. for two hours. A 1.0 ml aliquot of $PhHSiCl_2$, was added to each of four dried Pyrex Brand tubes and the tubes sealed. The tubes were then heated in a tube heater maintained at 300° C., for the times given in Table 1. At each indicated time period, a tube was removed from the tube heater and placed in dry ice to cool.

The content of each tube was evaluated using gas liquid chromatography (GLC) with a thermal conductivity (TC) detector. The results are present in Table 1 as the area percent under the GLC-TC readout curve, for each of the described compounds.

TABLE 1

Thermal Disproportionation of $PhHSiCl_2$ at 300° C.

| | GLC-TC Area % | | | | |
|---|---|---|---|---|---|
| Time (h) | $PhHSiCl_2$ | $H_2SiCl_2$ | $HSiCl_3$ | $PhSiCl_3$ | $Ph_2SiCl_2$ |
| 1.0 | 86.0 | 2.1 | 0.0 | 4.1 | 7.0 |
| 2.0 | 81.1 | 3.4 | 0.3 | 4.3 | 10.1 |
| 3.0 | 74.2 | 5.3 | 0.3 | 3.8 | 15.8 |
| 18.5 | 47.9 | 7.2 | 3.6 | 6.2 | 30.8 |

EXAMPLE 2

The thermal disproportionation of $PhHSiCl_2$ at 350° C. was evaluated by a process similar to that described for Example 1. The results are presented in Table 2.

TABLE 2

Thermal Disproportionation of $PhHSiCl_2$ at 350° C.

| | GLC-TC Area % | | | | |
|---|---|---|---|---|---|
| Time (h) | $PhHSiCl_2$ | $H_2SiCl_2$ | $HSiCl_3$ | $PhSiCl_3$ | $Ph_2SiCl_2$ |
| 1.0 | 61.6 | 8.0 | 1.0 | 4.1 | 23.7 |
| 2.0 | 55.7 | 9.1 | 1.6 | 4.2 | 27.4 |
| 3.0 | 45.2 | 8.4 | 4.3 | 5.6 | 32.3 |
| 15.0 | 27.9 | 4.4 | 7.6 | 17.8 | 34.8 |

EXAMPLE 3

The thermal disproportionation of $PhHSiCl_2$ at 400° C. was evaluated by a process similar to that described for Example 1. The results are presented in Table 3.

TABLE 3

Thermal Disproportionation of $PhHSiCl_2$ at 400° C.

| | GLC-TC Area % | | | | |
|---|---|---|---|---|---|
| Time (h) | $PhHSiCl_2$ | $H_2SiCl_2$ | $HSiCl_3$ | $PhSiCl_3$ | $Ph_2SiCl_2$ |
| 0.5 | 55.3 | 6.3 | 3.3 | 4.7 | 26.4 |
| 1.0 | 37.5 | 5.6 | 7.3 | 10.0 | 32.9 |
| 1.5 | 34.2 | 5.2 | 7.6 | 12.0 | 33.7 |
| 2.0 | 30.2 | 4.5 | 7.8 | 16.1 | 33.5 |

EXAMPLE 4

The thermal disproportionation of phenylmethylchlorosilane at 350° C., for one hour, was evaluated. The process was similar to that described for Example 1, except that the tubes were maintained under a nitrogen blanket after drying. The results were analyzed by GLC using both a flame ionization detector (FID) and a mass spectrometer (MS) as a detector. The results are presented in Table 4 as the area percent under the curve defined by the detector readout.

TABLE 4

Thermal Disproportionation of PhMeHSiCl

| GLC-TC Area % | | | | | |
|---|---|---|---|---|---|
| PhMeHSiCl | $PhMeSiH_2$ | $PhMeSiCl_2$ | $Ph_2MeHSi$ | $Ph_2MeSiCl$ | $(PhMeH)_2O$ |
| 19.4 | 1.5 | 2.4 | 1.1 | 36.2 | 29.3 |

EXAMPLE 5

(Not within the scope of the present invention) The thermal disproportionation of $PhHSiCl_2$ at various temperatures. in vapor phase, was evaluated. The process was conducted under a nitrogen gas blanket. Liquid $PhHSiCl_2$ was fed to a heated 2.5 cm by 33 cm quartz column packed with broken quartz. The flow rate of liquid $PhHSiCl_2$ to the heated column is presented in Table 5. The temperatures ranges evaluated by this process are described in Table 5. The eluent from the column was evaluated by GLC-TC and the results are present as area percent under the GLC-TC readout curve.

TABLE 5

Thermal Disproportionation of $PhHSiCl_2$ in The Vapor Phase

| Flow Rate (ml/min.) | Temp. Range (°C.) | GLC-TC Area % $Ph_2SiCl_2$ |
|---|---|---|
| 0.6 | 380–410 | 0.2 |
| 0.1 | 478–500 | 4.0 |
| 0.1 | 564–620 | 26.8 |

A comparison of these results with those provided in Examples 1-3 demonstrate that disproportionation of PhHSiCl$_2$ to Ph$_2$SiCl$_2$ occur more readily and at lower temperatures in the liquid phase.

What is claimed is:

1. A process for thermal disproportionation of arylhalosilanes, the process comprising: heating arylhalosilanes of formula $$R_cR^1_dH_fSiX_{4-c-d-f}$$

in liquid phase at a temperature within a range of about 250° C. to 450° C. for a reaction time of 0.1 to 18 hours, to effect disproportionation to product arylhalosilanes of formula $$R_cR^1_dH_fSiX_{4-c-d-f}$$

where each R is independently selected from a group consisting of alkyl radicals of 1 to 12 carbon atoms, each $R^1$ is independently selected from a group consisting of aryl radicals and substituted aryl radicals, X is a halogen atom selected from a group consisting of bromide, chloride, and iodide, $a=1$ or 2, $b=1$ or 2, $c=0$ or 1, $a+b+c=2$ or 3, $d=a+1$, and $f=b-1$.

2. A process according to claim 1, where the halogen atom is chloride.

3. A process according to claim 1, where the temperature is within a range of about 300° C. to 400° C..

4. A process according to claim 1, where the reaction time is about 0.5 to 4 hours.

5. A process according to claim 1, where the arylhalosilane is methylphenylchlorosilane and the product arylhalosilane is methyldiphenylchlorosilane.

6. A process according to claim 1, where the arylhalosilane is phenyldichlorosilane and the product arylhalosilane is diphenyldichlorosilane.

7. A process according to claim 1, where the product arylhalosilane is triphenylchlorosilane.

8. A process according to claim 1, where the process is conducted in a continuous-flow pressure coil.

9. A process for thermal disproportionation of phenyldichlorosilane, the process comprising:
heating phenyldichlorosilane in a liquid phase, at a temperature within a range of about 300° C. to 400° C., for a time within a range of about 0.5 to 4 hours, in a continuous-flow high pressure coil, to effect disproportionation to product diphenyldichlorosilane.

10. A process according to claim 9, where phenyldichlorosilane is separated from product diphenyldichorosilane by distillation and the separated phenyldichlorosilane is recycled to the process.

11. A process according to claim 1, where the arylhalosilane is methylphenylchlorosilane.

12. A process for thermal disproportionation of methylphenylchlorosilane, the process comprising:
heating methylphenylchlorosilane in a liquid phase, at a temperature within a range of about 300° C. to 400° C., for a time within a range of about 0.5 to 4 hours, in a continuous-flow pressure coil, to effect disproportionation to product diphenylmethylchlorosilane.

* * * * *